(12) United States Patent
Johann

(10) Patent No.: US 10,265,714 B2
(45) Date of Patent: Apr. 23, 2019

(54) METHOD AND DEVICE FOR PROVIDING A COMPOSITION CONTAINING HYALURONIC ACID

(71) Applicant: BWT Aktiengesellschaft, Mondsee (AT)

(72) Inventor: Jürgen Johann, Nußloch (DE)

(73) Assignee: BWT AKTIENGESELLSCHAFT, Mondsee (AT)

( * ) Notice: Subject to any disclaimer, the term of this patent is extended or adjusted under 35 U.S.C. 154(b) by 0 days.

(21) Appl. No.: 16/029,692

(22) Filed: Jul. 9, 2018

(65) Prior Publication Data

US 2018/0311689 A1 Nov. 1, 2018

Related U.S. Application Data

(60) Division of application No. 14/988,339, filed on Jan. 5, 2016, now Pat. No. 10,046,345, which is a
(Continued)

(30) Foreign Application Priority Data

Jul. 8, 2013 (DE) .................. 10 2013 213 335

(51) Int. Cl.
| | | |
|---|---|---|
| A47K 3/00 | (2006.01) | |
| B05B 7/24 | (2006.01) | |
| A61K 8/73 | (2006.01) | |
| A61Q 19/00 | (2006.01) | |
| A61Q 19/08 | (2006.01) | |

(Continued)

(52) U.S. Cl.
CPC ............. *B05B 7/2483* (2013.01); *A23L 2/44* (2013.01); *A23L 2/52* (2013.01); *A61K 8/735* (2013.01); *A61K 9/0014* (2013.01); *A61K 31/728* (2013.01); *A61Q 19/00* (2013.01); *A61Q 19/007* (2013.01); *A61Q 19/08* (2013.01);
(Continued)

(58) Field of Classification Search
CPC .................................. B05B 7/2483; A23L 2/44
USPC ............................................................. 4/615
See application file for complete search history.

(56) References Cited

U.S. PATENT DOCUMENTS

| 6,859,955 B2 | 3/2005 | Hudson |
| 2002/0017494 A1 | 2/2002 | Haase |

(Continued)

FOREIGN PATENT DOCUMENTS

| CN | 103006475 A | 4/2013 |
| DE | 20 2005 015 270 U1 | 12/2005 |

(Continued)

OTHER PUBLICATIONS www.Inga-Ro-Systems.Eu: "Umkehrosmose Wasseraufbereitung nach modernsten Standards," Jun. 13, 2013, XP055132878, URL: https://web.archive.org/web/20130613041434/http://www.inga-ro-systems.eu/.

(Continued)

*Primary Examiner* — Lauren A Crane

(74) *Attorney, Agent, or Firm* — Bose McKinney & Evans LLP

(57) ABSTRACT

The invention relates to methods and to a device for providing a composition containing hyaluronic acid, in particular for cosmetic or medical purposes. This disclosure teaches that hyaluronic acid can be stored in a dose-metering device and that potable water from a potable water network can be mixed with hyaluronic acid using the dose-metering device such that a composition containing hyaluronic acid is formed.

5 Claims, 2 Drawing Sheets

Related U.S. Application Data continuation of application No. PCT/EP2014/064188, filed on Jul. 3, 2014.

(51) Int. Cl.
*A23L 2/44* (2006.01)
*A23L 2/52* (2006.01)
*A61K 9/00* (2006.01)
*A61K 31/728* (2006.01)
*B05B 1/18* (2006.01)

(52) U.S. Cl.
CPC .......... *B05B 1/185* (2013.01); *A23V 2002/00* (2013.01); *A23V 2250/60* (2013.01); *A61K 2800/87* (2013.01)

(56) References Cited

U.S. PATENT DOCUMENTS

2004/0052746 A1 3/2004 Tamareselvy et al.

2008/0020096 A1 1/2008 Blum et al.
2010/0190742 A1 7/2010 Breton et al.

FOREIGN PATENT DOCUMENTS

| DE | 10 2009 001 343 A1 | 9/2010 |
| DE | 10 2012 108 227 A1 | 6/2013 |
| EP | 1 498 392 A2 | 1/2005 |
| EP | 2 532 252 A1 | 12/2012 |
| JP | 2003-277218 A | 10/2003 |
| RU | 2100100 C1 | 12/1997 |
| WO | WO 2006/070453 A1 | 7/2006 |

OTHER PUBLICATIONS

English Translation of the Interntional Preliminary Report on Patentability, PCT/EP2014/064188, dated Jan. 14, 2016.

METHOD AND DEVICE FOR PROVIDING A COMPOSITION CONTAINING HYALURONIC ACID

RELATED APPLICATIONS

This application is a divisional application of U.S. patent application Ser. No. 14/988,339, filed Jan. 5, 2016, now U.S. Pat. No. 10,046,345, which is a continuation of PCT/EP2014/064188, filed Jul. 3, 2014, which claims priority to DE 10 2013 213 335.9, filed Jul. 8, 2013, all of which are incorporated herein by reference in their entirety.

BACKGROUND

The invention relates to a method and a device for providing a composition containing hyaluronic acid, in particular for cosmetic or medical purposes.

In chemical terms, hyaluronic acid is glycosaminoglycan. Hyaluronic acid, like all glycosaminoglycans, is composed as a macromolecular chain of repeating sugar units (disaccharides). In this connection, up to 100 000 such building blocks can follow one another and thus form the classic hyaluron compound. If the molecule is hydrated (i.e., it is joined to water), it expands and occupies up to 10 000 times more space than in its basic state. Thus, for example one gram of hyaluronic acid can store up to six liters of water. This expansion is visible through a gel-like appearance. Hyaluronic acid is thus an excellent water-binder.

Hyaluronic acid molecules, which are long and large and have high viscosity (lubrication) and/or pressure resistance, make it possible for the joints and the skin to carry the weight and/or to withstand stresses. Particularly large proportions of hyaluronic acid can be found in particular in joint cartilage, in the vitreous body of the eye and in many tissues in the body which have in particular a stabilizing task. Depending on in which expansion the hyaluronic acid is present, as well as a soft state, it is also possible to achieve a more viscous, more hard-rubber-like state which has the property that great pressure is cushioned. Furthermore, the structure of hyaluronic acid has a shaping and directional property, i.e., hyaluronic acid occurs at most places of the body where it is important that a certain hold or a shape is retained. Ultimately, hyaluronic acid is present in most human cells and ensures the structure and stability of the cell wall.

Hyaluronic acid is also a natural constituent of the skin. It effectively binds moisture in the upper layer of the skin. Its moisture-binding effect arises from the fact that it only releases its hydrate mantle gradually and, in so doing, acts on the skin over a long period. Its optical skin-tightening and smoothing effect results from the evaporation of water and the slight tightening of the gel film on the skin brought about as a result. The production of endogenous hyaluronic acid decreases with increasing age; this results in skin ageing phenomena, increased wrinkling, dry skin and loss of elasticity.

In this connection, it is known in the cosmetics industry to use hyaluronic acid in creams or gels, i.e., the hyaluronic acid is formulated in combination with many other ingredients, such as for example oils, fats, stearic acid or stearins, glycerol, silicates, etc. The massaging of the creams into the skin requires a certain effort and also leaves behind greasy residues of the carrier substance.

SUMMARY

Proceeding from this, this disclosure further improves the methods and devices known in the prior art for producing or providing hyaluronic acid, especially for cosmetic and medical purposes, and in so doing brings about an effective and simple application.

This disclosure proceeds from the concept of enabling natural absorption, especially on the skin, by adding hyaluronic acid to potable water. Accordingly, from a method point of view, it is proposed that hyaluronic acid is stocked in a metering device and that potable water taken from a potable water network is admixed with hyaluronic acid by means of the metering device, with formation of the composition. As a result, the hyaluronic acid can be absorbed in the skin very simply and with great effect, with the potable water free from residues. The water softens the skin, it becomes more permeable and as a result hyaluronic acid better penetrates into the skin. The effect of film formation on the skin and the smoothing of the skin is directly visible and detectable.

Thus, for example, during showering, hyaluronic acid can be metered into the shower water, the metering expediently taking place after soaping. The hyaluronic acid is absorbed with the water via the skin and forms a pleasantly acting film on the skin. The metering of hyaluronic acid into the shower or process water taken from the potable water network thus renders the laborious rubbing in of cream after showering unnecessary. The application is simple and only hyaluronic acid is absorbed by the skin. Particularly when showering with water temperatures of usually more than 30° C., the hyaluronic acid better penetrates into the skin.

However, the provision of hyaluronic acid in potable water is not only limited to external applications, but also encompasses oral consumption for nourishment of the body matrix. No additional ingredients have to be formulated for this either.

The metering process can be configured particularly easily by the potable water being passed as a flow through the metering device, with uptake of hyaluronic acid.

Handling is facilitated if the liquid composition formed from potable water and hyaluronic acid is discharged via a water outlet fittings, in particular in a shower, bath or a washbasin, for use on the skin.

In order to simplify oral administration, it is advantageous if the potable water is poured into a container containing the metering device for providing beverages.

The hyaluronic acid is advantageously metered into the potable water in a concentration in the range from 2 to 2000 mg/l.

Further advantageous embodiments provide for low molecular weight hyaluronic acid with a molecular weight <400 000 Daltons or high molecular weight hyaluronic acid with a molecular weight greater than 1 000 000 Daltons being metered into the potable water. For the external film formation, usually high molecular weight hyaluronic acid is used, while the metering of low molecular weight hyaluronic acid facilitates penetration through the epidermis, such that the hyaluronic acid can be stored in the dermis.

In order to avoid a buildup of germs in the metering device, it is advantageous if the hyaluronic acid is admixed with a preservative, in particular sorbic acid or silver resin. In this connection, the sorbic acid can be mixed or introduced into hyaluronic acid in particular in the form of a powder or tablet, in which case the sorbic acid concentration should be about 0.2%. For preservation with silver, silver resin can be mixed with hyaluronic acid, with a concentration of about 1% silver resin.

With regard to a device for providing a composition containing hyaluronic acid, the improvement specified at the start is achieved by a metering device containing hyaluronic acid which can be supplied with potable water from a potable water network, where the composition is formed from potable water and hyaluronic acid. The advantageous effects already specified in connection with the method arise to an equal extent here. Analogous features and measures can therefore also be combined accordingly.

In order to reduce structural expenditure and to facilitate handling, it is advantageous if the metering device has a pressure connection for introducing potable water under pressure.

In order to also reduce maintenance expenditure, it is advantageous if the metering device has an interchangeable cartridge containing hyaluronic acid.

Undesired back-flow can be avoided by arranging a non-return valve in the inlet and outlet of the interchangeable cartridge.

For a targeted observing of metering amounts, it is advantageous if the metering device has a metering pump for metering liquid or a metering lock for metering solids.

Further use advantages arise as a result of the fact that the metering device is switchable via a reversing valve as required for supplying the composition or potable water.

This disclosure also provides the use of a composition of potable water and hyaluronic acid for treating skin.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
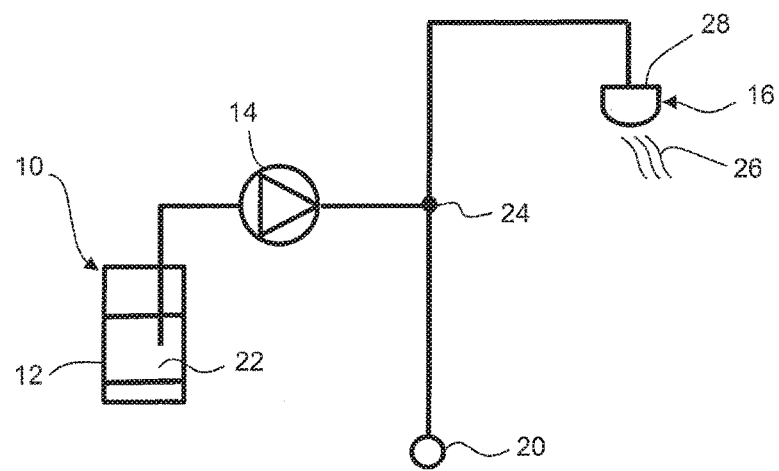
FIG. 1 is a block diagram of a device for providing hyaluronic acid for treating skin.

The device shown in FIG. 1 comprises a metering device 10 with storage container 12 and metering pump 14, as well as a shower 16 with showerhead 28 and pressure connection 20 for potable water. The storage container 12 contains an aqueous hyaluronic acid solution 22 which can be metered into the drawn potable water by means of the metering pump 14 at the branching point 24. The composition of potable water and hyaluronic acid 26 can then be applied to the skin as required via the showerhead 28 during showering.

Figure 2:
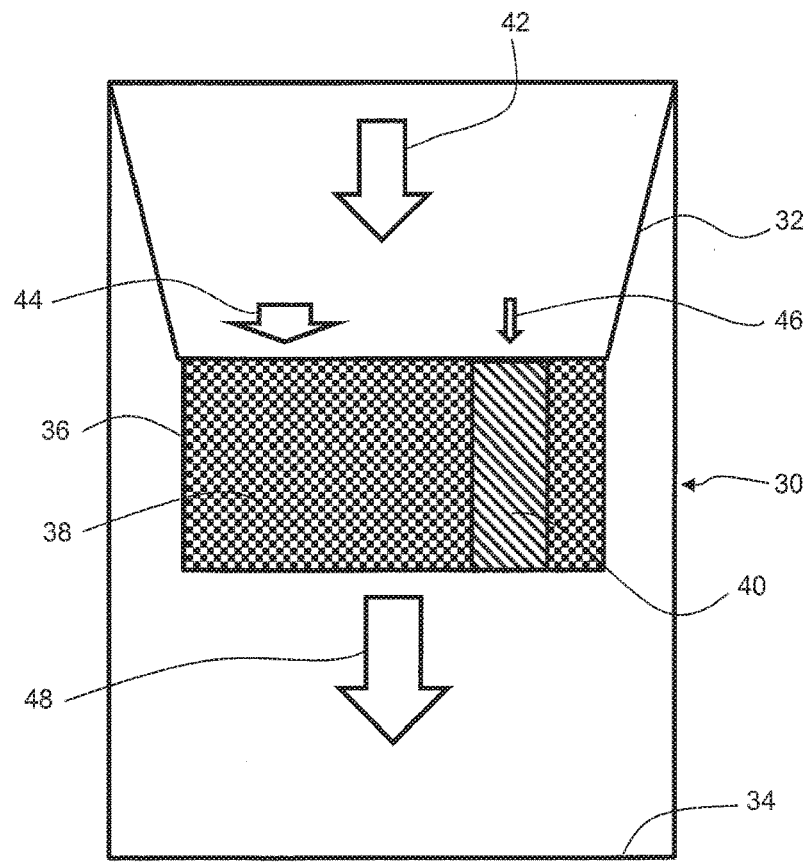
FIG. 2 is a diagrammatically simplified representation of a device for providing hyaluronic acid in a potable water jug.

The metering device according to FIG. 2 has a water jug (pitcher) 30 which comprises an upper funnel section 32, a collecting section 34 on the floor and a filter cartridge 36 at the outlet of the funnel section 32. The filter cartridge 36 contains a bed 38 of a filter material and a cartridge insert 40 with hyaluronic acid as solid.

The potable water 42 drawn from a potable water network (not shown) is poured into the funnel section 32, where, under the influence of gravity, a main stream 44 is for example decalcified through the filter material 38, whereas a part stream 46 passes through the cartridge insert 40 and in so doing is enriched with hyaluronic acid. The composition 48 of filtered potable water and hyaluronic acid is then collected in the floor section 34 and can from there be poured into a drinking container via an outlet (not shown) as required.

Figure 3A:
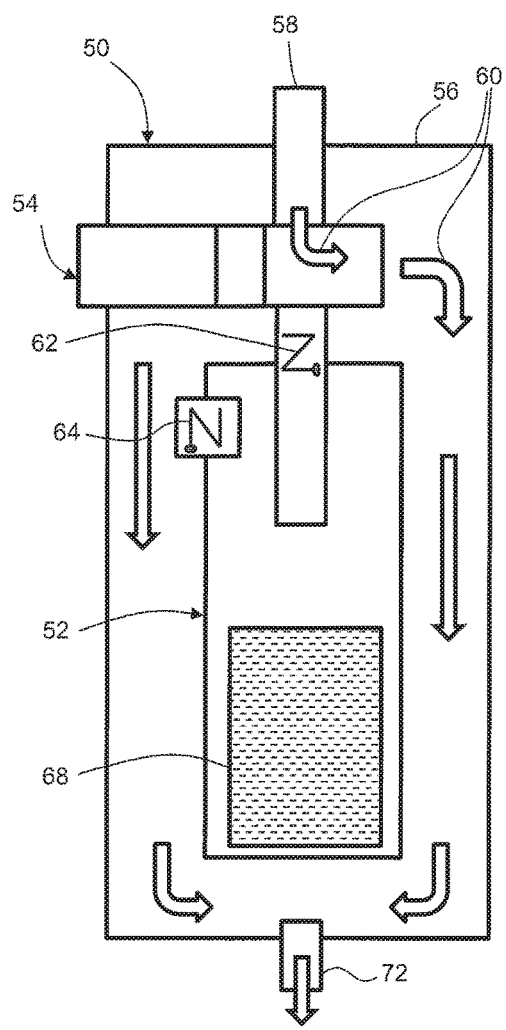
FIGS. 3a and b are block diagrams of a metering device containing hyaluronic acid in a lock position and a demand position, respectively.
Figure 3B:
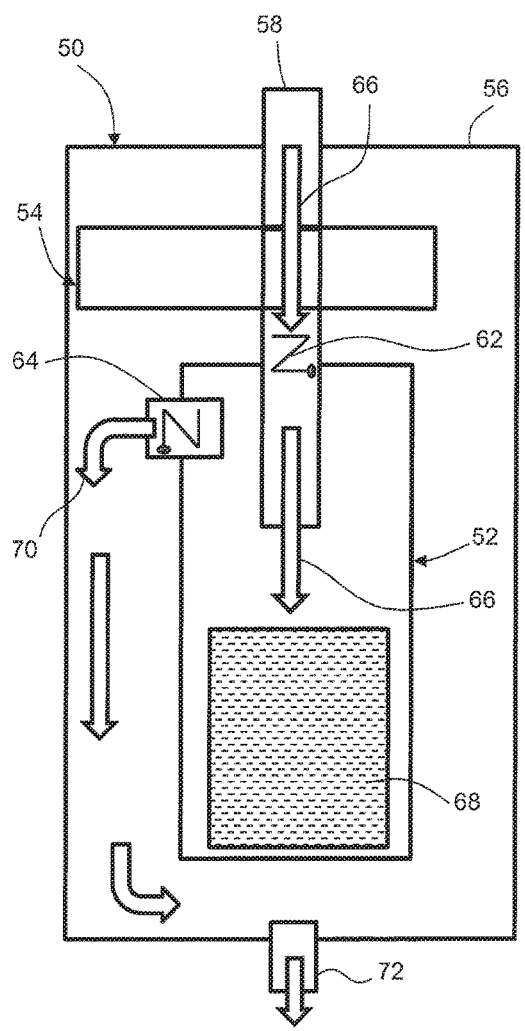

FIGS. 3a and 3b show a further embodiment of a metering device 50 with a metering lock 52 for hyaluronic acid and a reversing valve 54 in a receiving container 56 for the on-demand metering in of the hyaluronic acid.

In the switch position of the reversing valve 54 shown in FIG. 3a, only the receiving container 56 is supplied with pressurized water via the potable water connection 58 in the direction of the flow arrow 60, whereas the metering lock 52 remains blocked at the inlet and outlet by non-return valves 62, 64. The non-return valve 62 here prevents a back-flow via the inlet into the potable water flow 60, and the non-return valve 64 blocks the outlet against penetration of potable water from the surrounding container space.

In the switch position of the reversing valve 54 shown in FIG. 3b, the potable water connection 58 is connected with the inside space of the metering lock 52, where the potable water flows through the non-return valve 62 in the direction of the flow arrow 66 and comes into contact with the solid bed 68 of hyaluronic acid. The composition of potable water and hyaluronic acid then flows from the metering lock 52 via non-return valve 64 into the receiving container (flow arrow 70) and can then be drawn off at the container exit 72. The metering device 50 can be incorporated into the feedline of a water outlet fixture, e.g., a shower, with the solid bed 68 expediently being formed by an interchangeable cartridge.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A device for providing a composition containing hyaluronic acid, the device comprising:
   a container containing hyaluronic acid;
   an inlet configured to connect to a potable water source under pressure to receive potable water; and
   a meter configured to feed hyaluronic acid from the container into the potable water received from the potable water source to thereby form a composition from potable water and hyaluronic acid, the composition being configured to be discharged via a showerhead of a shower for use on the skin, further wherein the meter is configured to meter the hyaluronic acid into the potable water in a concentration range of from 2-2000 mg/l.

2. The device as claimed in claim 1, wherein the container has an interchangeable cartridge containing hyaluronic acid.

3. The device as claimed in claim 2, wherein the container has a first non-return valve to prevent backflow into the potable water source and a second non-return valve to prevent flow of potable water into the cartridge.

4. The device as claimed in claim 1, wherein the meter has a metering pump for metering liquid or a metering lock for metering solids.

5. The device as claimed in claim 1, further comprising a reversing valve configured for switching on and off the feed of hyaluronic acid.

\* \* \* \* \*